United States Patent [19]

Kaneyasu et al.

[11] Patent Number: 4,586,143
[45] Date of Patent: Apr. 29, 1986

[54] GAS DETECTING APPARATUS

[75] Inventors: Masayoshi Kaneyasu; Takanobu Noro; Hideo Arima, all of Yokohoma; Mitsuko Ito, Yokosuka; Shoichi Iwanaga, Yokohama; Nobuo Sato, Yokosuka; Akira Ikegami, Yokohama; Tokio Isogai, Fujisawa, all of Japan

[73] Assignee: Hitachi, Ltd., Tokyo, Japan

[21] Appl. No.: 461,743

[22] Filed: Jan. 28, 1983

[30] Foreign Application Priority Data

Mar. 24, 1982 [JP] Japan .................... 57-45602

[51] Int. Cl.[4] .................... G01N 27/12
[52] U.S. Cl. .................... 364/509; 73/23; 340/634; 364/497
[58] Field of Search .................... 364/497–500, 364/502, 509; 73/23, 27 R; 422/98; 340/634; 324/71.5

[56] References Cited

U.S. PATENT DOCUMENTS 4,432,224 2/1984 Typpo .................... 73/23
4,457,161 7/1984 Iwanaga et al. .................... 73/23
4,481,499 11/1984 Arima et al. .................... 73/23

OTHER PUBLICATIONS

Clifford, P. K. et al, "Research Progresses Toward a Selective MOS Gas Sensor", Industrial Research & Development, Apr. 1982, pp. 143–147.

Primary Examiner—Errol A. Krass
Assistant Examiner—Heather Rherndon
Attorney, Agent, or Firm—Antonelli, Terry & Wands

[57] ABSTRACT

A gas detecting apparatus is disclosed in which detection outputs from a plurality of semiconductor gas detecting elements different in gas detection characteristic from each other and previously-obtained characteristic values of the semiconductor gas detecting elements for a mixed gas are subjected to operational processing to detect one or more specified constituent gases contained in the mixed gas, and in which when the specified constituent gas is detected, the detection information is announced by some means, and also the supply of gas is stopped or a supply gas is diluted.

9 Claims, 29 Drawing Figures

GAS DETECTING APPARATUS

The present invention relates to a gas detecting apparatus for obtaining gas information such as respective concentrations of known constituent gases contained in a mixed gas, and more particularly to a gas detecting apparatus which can eliminate a malfunction caused by an interfering gas such as alcohol vapor.

Semiconductive materials such as tin oxide ($SnO_2$), iron oxide ($Fe_2O_3$) and zinc oxide ($ZnO$) have been widely used to detect gas, since these materials are inexpensive, and since semiconductor gas detecting elements made of these materials are easy to use. The operation principle of a semiconductor gas detecting element is as follows. The conductivity of the semiconductor gas detecting element (hereinafter referred to as the element conductivity) is varied by the electron exchange between absorbed oxygen at an active portion of the element and gas to be detected, and the variation in element conductivity is converted into a voltage output by a detection circuit. FIG. 1 shows an example of the detection circuit. In FIG. 1, reference numeral 11 designates a gas detecting element, 12 a fixed resistor, and 13 a detecting voltmeter.

FIG. 2 shows detection characteristics of a semiconductor gas detecting element made of $SnO_2$. In FIG. 2, curves 14, 15, 16 and 17 indicate detection characteristics of the element for alcohol vapor, hydrogen, carbon monoxide and methane, respectively. As shown in FIG. 2, a specified functional relation exists between the concentration of detection gas and the element conductivity, and therefore the semiconductor gas detecting element is put to practical use.

The exhaust gas from automobiles and the leakage of gas in chemical plants have recently become a social issue. In order to detect the above gases, techniques for determining respective concentrations of constituent gases contained in a mixed gas are required. However, conventional semiconductor gas detecting elements have the following drawbacks. First, a detecting element made of zinc oxide containing palladium for detecting hydrogen will be explained, by way of example. FIG. 3 shows detection characteristics of this element. In FIG. 3, curves 21, 22 and 23 indicate detection characteristics of the element for hydrogen, carbon monoxide and propane, respectively. As shown in FIG. 3, the element is sensitive to the three gases. Accordingly, the detection output of the element for a mixed gas containing the three gases is nearly equal to the sum of the detection outputs for these constituent gases, and therefore the detection accuracy for hydrogen is lowered in a large degree. This phenomenon is considered to result from the fact that the amount of absorbed hydrogen is varied by the absorption of other gases than hydrogen. That is, the phenomenon is more or less observed in any gas detecting material, and therefore is a serious drawback of conventional semiconductor gas detecting elements.

Further, a detecting element made of $SnO_2$ for detecting methane has the same property as the above-mentioned, though this element is generally used in gas alarms on the market. That is, this element is sensitive to not only methane but also other gases. Especially, the detection output of the element for alcohol vapor is equal to or more than that of the element for methane contained in the same concentration as alcohol vapor. Alcohol vapor is produced in general living facilities with high frequency, that is, is produced in cooking and drinking. Accordingly, the detection of alcohol vapor is often mistaken for the detection of methane, and thus an alarm is generated. Such a malfunction is another serious drawback of conventional semiconductor gas detecting elements.

An object of the present invention is to provide a precise, inexpensive gas detecting apparatus which can eliminate the above-mentioned drawbacks of the prior art and can rapidly obtain gas information such as respective concentrations of known constituent gases contained in a mixed gas.

Another object of the present invention is to provide a gas detecting apparatus which can perform the above-mentioned operation notwithstanding a gas detecting element having an exponential detection characteristic is employed.

A gist of the presnet invention is to utilize the fact that a characteristic value determining a relation between the detection output of a semiconductor gas detecting element (hereinafter referred to as a "detecting element") and the concentration of detection gas, namely, a detection characteristic value varies with detecting element and detection gas. That is, when N kinds of gases are to be detected, N detecting elements different from each other in detection characteristic value for each of the N detection gases are used, and the detection characteristic value of each detecting element for each detection gas is previously measured. Then, N simultaneous linear equations are formed by using detection outputs measured by the detecting elements and coefficients each calculated from the previously-measured detection characteristic value of each detecting element for each detection gas (hereinafter referred to as "characteristic coefficients"). The simultaneous equations are solved to obtain gas information such as the kind and concentration of each of consituent gases contained in a mixed gas, the concentration ratio of constituent gases, and the presence or absence of a specified gas.

The present invention will be apparent from the following detailed description taken in conjunction with the accompanying drawings, in which:

FIG. 5b is a sectional view taken along the line Vb of FIG. 5a;

FIG. 18b is a sectional view taken along the line XVIII$_b$ of FIG. 18a;

Figure 1:
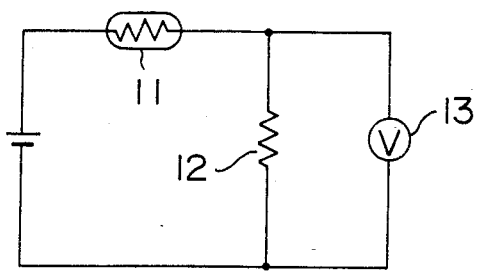
FIG. 1 is a circuit diagram showing a detection circuit of a conventional semiconductor gas detecting element.
Figure 2:
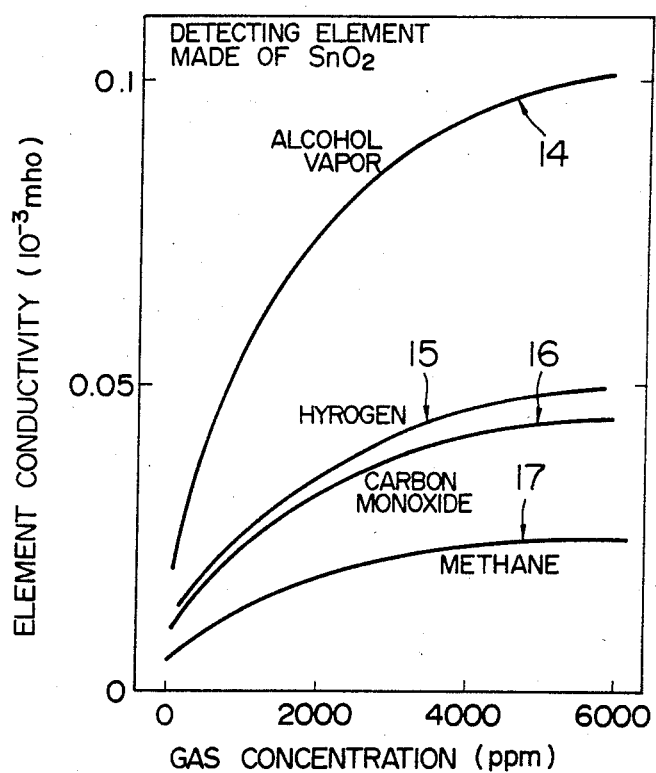
FIG. 2 is a graph showing examples of the relation between the concentration of gas and the element conductivity obtained by the detection circuit shown in FIG. 1 (hereinafter referred to as "detection characteristic")
Figure 3:
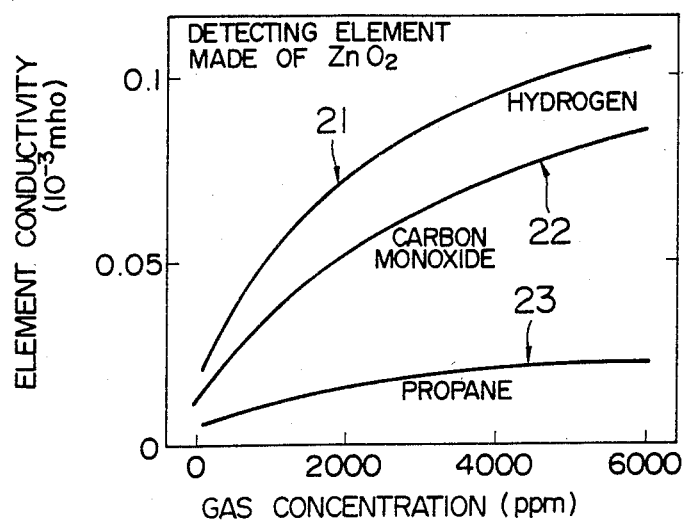
FIG. 3 is a graph showing the detection characteristic of a hydrogen detecting element made of zinc oxide (ZnO) containing palladium for hydrogen and other gases.
Figure 4A:
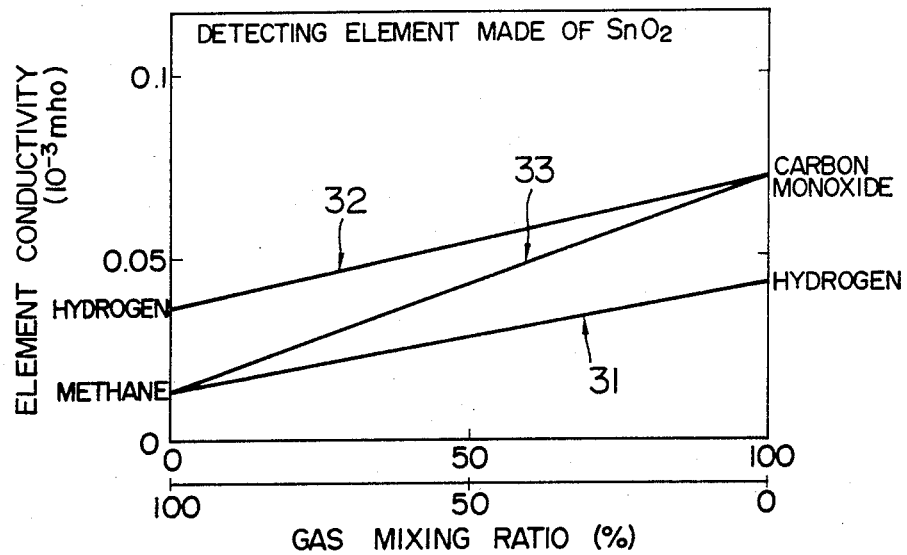
FIG. 4a is a graph showing the detection characteristic of a detecting element made of $SnO_2$ for a mixed gas containing methane, hydrogen and carbon monoxide.

When a detecting element is exposed to a mixed gas containing specified kinds of constituent gases, the conductivity of the detecting element varies linearly with the mixing ratio of the constituent gases as shown in FIG. 4a. In FIG. 4a, a straight line 31 indicates the variation of the conductivity of a detecting element made of $SnO_2$ with the mixing ratio of methane and hydrogen, a straight line 32 the variation of the conductivity of the detecting element with the mixing ratio of hydrogen and carbon monoxide (CO), and a straight line 33 the variation of the element conductivity with the mixing ratio of CO and methane. In such a case, the concentration of each constituent gas can be determined if the mixing ratio of constituent gases in a mixed gas is known.

Figure 4B:
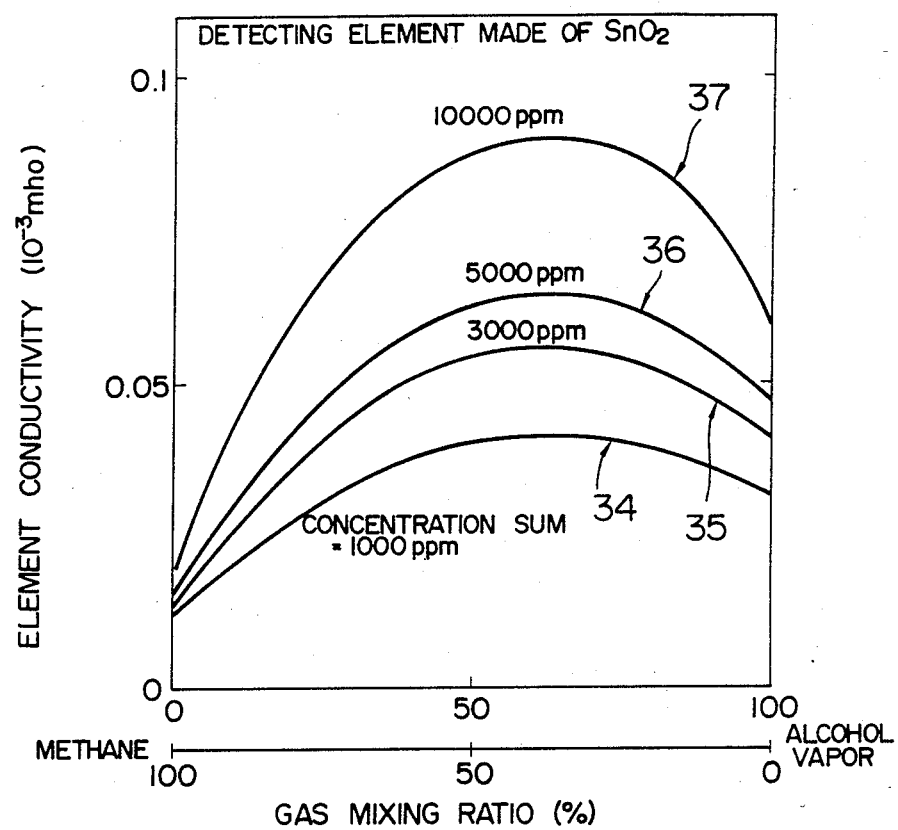
FIG. 4b is a graph showing the detection characteristic of the detecting element made of $SnO_2$ for a mixed gas containing methane and alcohol vapor.

In the case where a mixed gas contains alcohol vapor, the element conductivity varies non-linearly with the mixing ratio of constituent gases as shown in FIG. 4b, and therefore it is very difficult to determine the concentration of each constituent gas. In FIG. 4b, curves 34, 35, 36 and 37 indicate the detection characteristic of the detecting element made of $SnO_2$ for mixed gases containing methane and alcohol vapor at total concentrations of 1,000, 3,000, 5,000 and 10,000 ppm. Such phenomenon is considered to result from the following fact. That is, gas molecules of methane, hydrogen and CO make the exchange of electron mainly with oxygen which is absorbed by an active surface of a detecting element in the form of a negative ion $O^-$. On the other hand, alcohol vapor makes the exchange of electron with oxygen absorbed by the active surface in the form of another negative ion $O^{2-}$. In other words, respective effects of methane, hydrogen and CO on the detection output of the detecting element can be added to each other, since these gases make the exchange of electron mainly with the absorbed ion $O^-$. In the case where alcohol vapor is contained in a mixed gas in addition to the above gases, however, the effect of these gases and that of alcohol vapor on the detection output of the detecting element are multiplied by each other, since the gases make electron exchange with the absorbed ion $O^-$ and the alcohol vapor makes electron exchange with the absorbed ion $O^{2-}$. Accordingly, the detecting element has a nonlinear detection characteristic for a mixed gas containing alcohol vapor.

However, according to a method in which the effect of alcohol vapor on the detection characteristic of a detecting element is expressed by a function and then the effect of alcohol vapor on the detection output of the detecting element is removed by calculation as in an embodiment of the present invention mentioned later, the effect of only constituent gases whose mixing ratio is proportional to the conductivity of the detecting element, on the detection output of the detecting element can be calculated, and thus the concentration of each of these constituent gases can be determined.

In order to facilitate the understanding of the present invention, a basic principle thereof will be briefly explained. The fundamental technical thought of the present invention is to utilize the fact that the effects of respective concentrations of specified constituent gases on the conductivity of a detecting element can be added to each other. That is, a characteristic coefficient $a_{ij}$ of an i-th detecting element for a j-th specified detection gas having a concentration C is calculated by the following equation:

$$a_{ij} = g_{ij}(C)/C \qquad (1)$$

where $g_{ij}(C)$ indicates the conductivity of the i-th detecting element caused by the j-th detection gas having the concentration C.

The element conductivity $g_{ij}(C)$ is calculated by the following equation:

$$g_{ij}(C) = k_{ij}(C+l_{ij})^{m_{ij}} \qquad (2)$$

where $k_{ij}$, $l_{ij}$ and $m_{ij}$ are characteristic values in expressing the variation of the conductivity of the i-th detecting element with the concentration of the j-th detection gas by a function of the concentration C. Accordingly, the characteristic coefficient $a_{ij}$ can be varied by changing the material of the i-th detecting element. A conductivity $G_i$ of the i-th detecting element exposed to a mixed gas is given by the following equations:

$$G_i = \sum_{j=1}^{N} a_{ij} \cdot C_j \qquad (3)$$

$$= \sum_{j=1}^{N} \{g_{ij}(C)/C\} \cdot C_j \qquad (4)$$

where $$C = \sum_{j=1}^{N} C_j,$$

and where N indicates the number of constituent gases contained in the mixed gas and $C_j$ the concentration of the j-th constituent gas.

The processing in the case where the sum of respective concentrations of constituent gases is not known, will be explained in EMBODIMENT III. Accordingly, let us consider the case where the sum of respective concentrations of constituent gases is known. When a characteristic coefficient matrix A is given by an N×N matrix in which a characteristic coefficient $g_{ij}(C)/C$ determined by the sum C of respective concentrations of constituent gases is an element in the i-th row, j-th column, the concentration $C_j$ of the j-th constituent gas is calculated by a known method of solving simultaneous linear equations, and is expressed by the following equation:

$$C_j = \frac{1}{\det A} \sum_{j=1}^{N} q_{ij} G_i \quad (5)$$

where det A indicates the determinant of the matrix A, and $q_{ij}$ is an element in the i-th row, j-th column of the adjunct matrix of the matrix A.

In brief, the concentration $C_j$ of the j-th constituent gas of a mixed gas to be measured can be univocally determined in the following manner. That is, detecting elements made of different materials, the number of which is equal to the number of constituent gases, are exposed to the mixed gas, and then the conductivity of each detecting element is measured. The concentration of each constituent gas is determined, by matrix calculation, on the basis of the measured element conductivity. Moreover, the above calculation can be carried out by a microcomputer which previously stores therein characteristic values included in functions indicating the detection characteristic of each detecting element for each constituent gas, and therefore real time processing can be performed.

According to the prior art, the i-th detecting element is made of a material which can make extremely large the characteristic coefficient $g_{ij}(C)/C$ for the j-th, important constitutent gas of a mixed gas to be measured, and the effect of other constituent gases on the element conductivity is treated as an error and corrected appropriately to obtain an approximate concentration value of the j-th constituent gas. On the other hand, according to the present invention, the characteristic coefficient $g_{ij}(C)/C$ for the j-th, important constituent gas is made relatively large to improve detection accuracy, and the effect of other constituent gases on the element conductivity is not neglected but utilized to determine respective concentrations of other constituent gases. That is, the present invention differs from the prior art in this point.

Now, five embodiments of a gas detecting method and a gas detecting apparatus according to the present invention will be explained below in detail, with reference to the drawings. The contents of these embodiments are as follows:

EMBODIMENT I shows a structure of a sensor unit having six sensors and a method of processing detection outputs; EMBODIMENT II shows other structures of sensor unit; EMBODIMENT III shows an apparatus for and a method of processing detection outputs obtained by EMBODIMENT's I and II; EMBODIMENT IV shows a method of forming a 3-element sensor unit capable of determining respective concentrations of methane, CO and alcohol vapor; and EMBODIMENT V shows an apparatus for and a method of processing detection outputs obtained by EMBODIMENT IV.

EMBODIMENT I

Figure 5A:
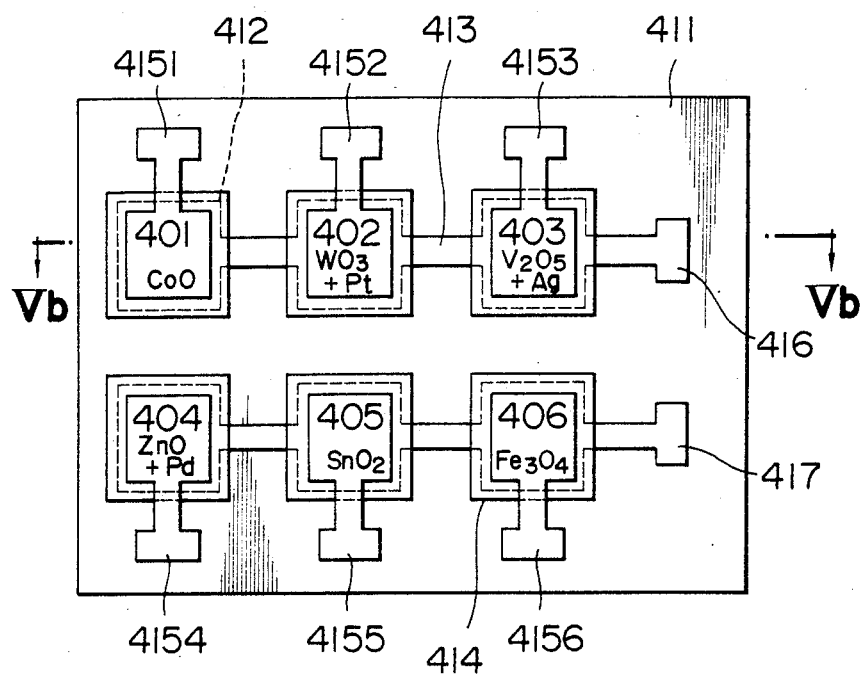
FIG. 5a is a schematic plan view showing a detecting element part according to a first embodiment of the present invention which includes six sensors.

FIG. 5a is a schematic plan view showing a gas detecting element part which is a main part of a mixed-gas detecting apparatus according to the present invention. The gas detecting element part includes six detecting elements (hereinafter referred to as "sensors") 401 to 406 which are arranged in the form of a matrix. These sensors are formed in the following manner. First, gold paste (for example, paste No. 8760 manufactured by Dupont Co.) is applied to a heat-resisting, insulating substrate 411 through the well-known thick film printing technique, to form six lower electrodes 412 at predetermined positions and to form connecting conductors 413 for connecting lower electrodes 412. Then, six kinds of gas sensitive paste 414 which are different from each other in gas detection characteristic, are applied to the lower electrodes 412 to a predetermined thickness (for example, about 10 μm) thorugh the thick film printing technique. At this time, each of six kinds of gas sensitive paste is applied to a corresponding one of the lower electrodes. Further, upper electrodes 415 each having a predetermined size and a predetermined shape are formed on the gas sensitive paste 414 through the printing technique. Then, the above structure is held at a firing temperature of 900° C. for 10 minutes. Thus, a sensor unit for analyzing a multi-component gas is completed which includes six sensors each having a sandwich structure, and predetermined wiring.

Next, the six kinds of gas sensitive paste for realizing the technical thought of the present invention will be explained below. The sensors 401 to 406 in the present embodiment are formed as follows. Cobalt oxide CoO is used to form the gas sensitive paste for the sensor 401, a mixture of $WO_3$ and Pt is used to form the paste for the sensor 402, a mixture of $V_2O_5$ and Ag is used to form the paste for the sensor 403, a mixture of ZnO and Pd is used to form the paste for the sensor 404, tin oxide $SnO_2$ is used to form the paste for the sensor 405, and iron oxide $Fe_3O_4$ is used to form the paste for the sensor 406. Each of these materials is mixed with crystallized glass having a high melting point substantially in a ratio of 1:0.1 by weight. The mixture thus obtained is slurried with an organic binder to form desired paste.

Figure 5B:
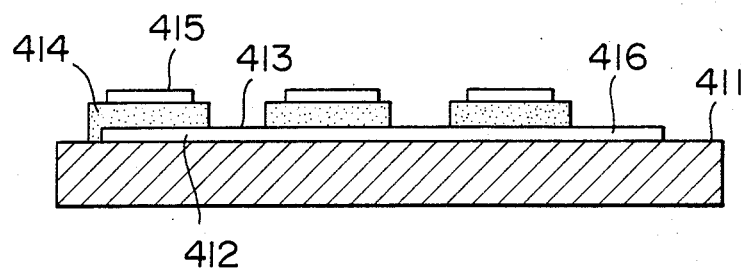

Signals (namely, signal voltages) from the gas detecting element part having the above-mentioned structure are taken out by the upper electrodes 415 and lower electrodes 412. For example, the signal generated by the sensor 402 is taken out by a lower electrode terminal 416 in the first row and an upper electrode terminal 4152 in the second column. That is, all of the signals from the gas detecting element part can be taken out by scanning rows and columns of the upper and lower electrodes arranged in the form of a matrix. FIG. 5b is a sectional view of the gas detecting element part, taken along the line V of FIG. 5a. FIGS. 6 to 11 are graphs for showing measured output voltages of the sensors 401 to 406 shown in FIG. 5a for oxygen, hydrogen, nitrogen dioxide, carbon monoxide, hydrocarbons and water vapor.

Figure 6:
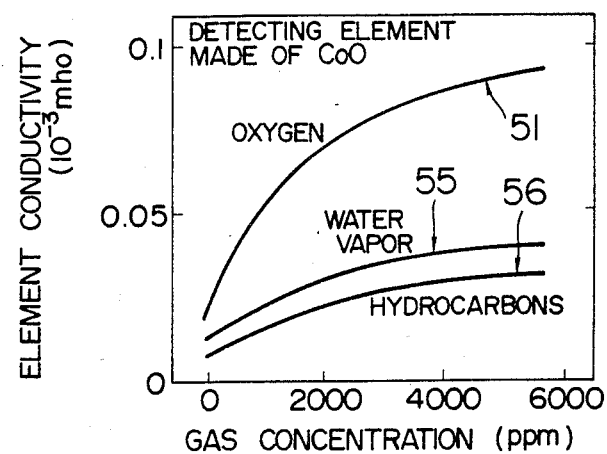
FIGS. 6 to 11 are graphs showing the detection characteristic of each of the six sensors shown in FIG. 5a for a mixed gas containing six constituent gases.
Figure 7:
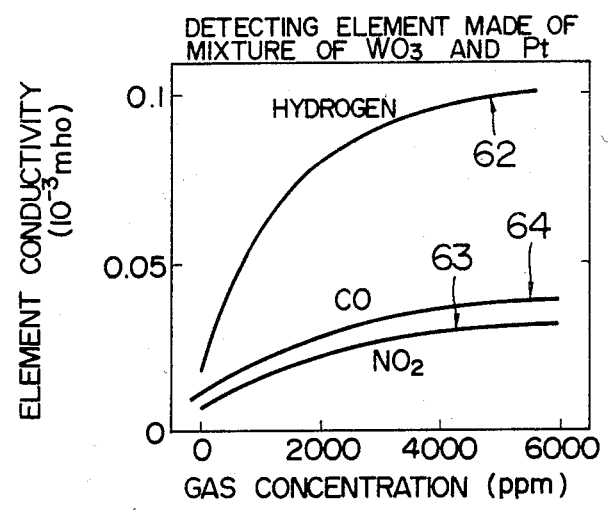
Figure 8:
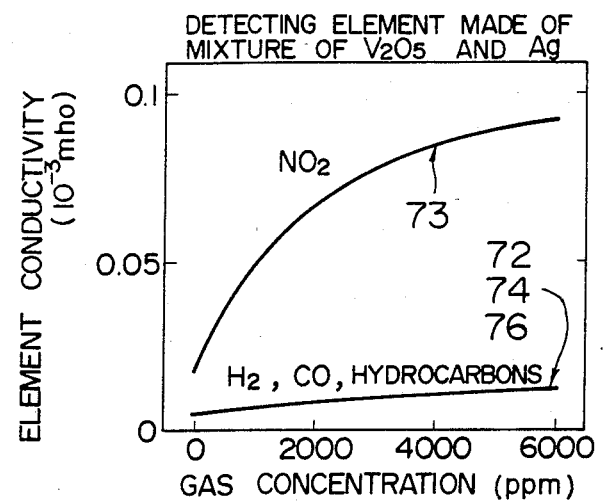
Figure 9:
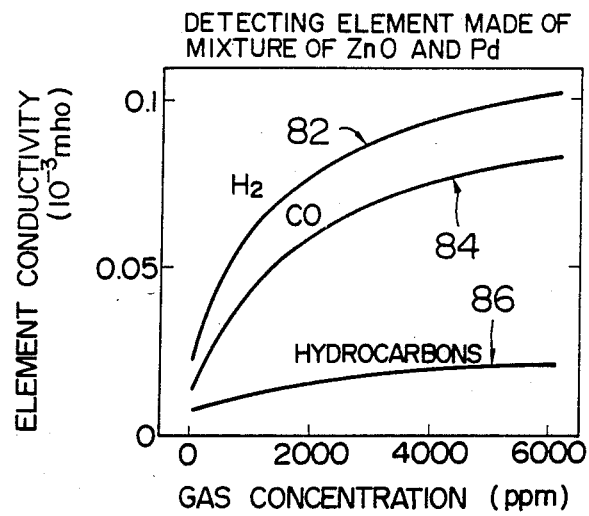
Figure 10:
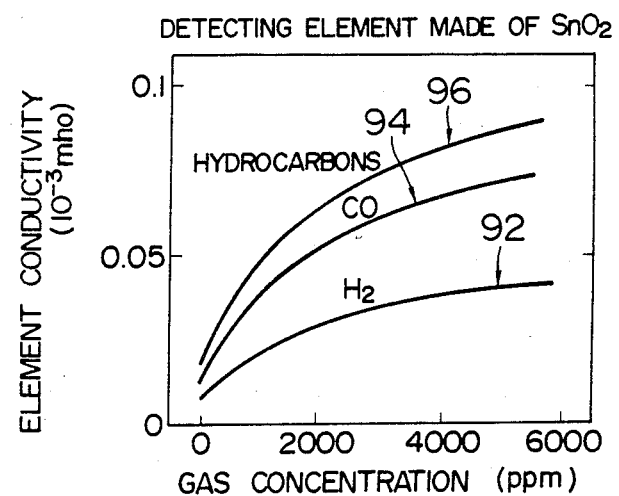
Figure 11:
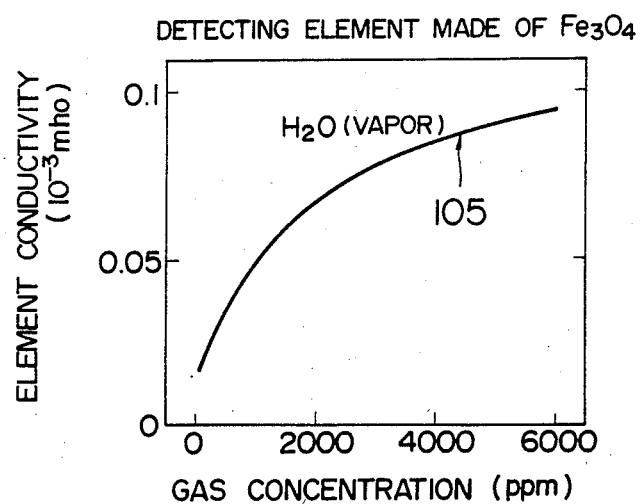

In FIG. 6, a curve 51 indicates a detection output characteric of the sensor 401 made of CoO for oxygen $O_2$, and curves 55 and 56 indicate a detection output characteristic of the sensor 401 for water vapor $H_2O$ and that for hydrocarbons, respectively. In FIG. 7, a curve 62 indicates a detection output characteristic of the sensor 402 made of a mixture of $WO_3$ and Pt for hydrogen $H_2$, and curves 63 and 64 indicate a detection output characteristic of the sensor 402 for nitrogen dioxide $NO_2$ and that for carbon monoxide CO, respectively. In FIG. 8, a curve 72 indicates a detection output characteristic of the sensor 403 made of a mixture of $V_2O_5$ and Ag for $H_2$, and curves 73, 74 and 76 indicate a detection output characteristic of the sensor 403 for $NO_2$, and those for CO and hydrocarbons, respectively. In FIG. 9, a curve 82 indicates a detection output characteristic of the sensor 404 made of a mixture of ZnO and Pd for $H_2$, and curves 84 and 86 indicate a detection output characteristic of the sensor 404 for CO and that for hydrocarbons, respectively. In FIG. 10, a curve 92 indicates a detection output characteristic of the sensor 405 made of $SnO_2$ for $H_2$, and curves 94 and 96 indicate a detection output characteristic of the sensor 405 for CO and that for hydrocarbons, respectively. In FIG. 11, a curve 105 indicates a detection output characteristic of the sensor 406 made of $Fe_3O_4$ for water vapor.

Now, explanation will be made on the case where a mixed gas containing six constituent gases is analyzed by the above-mentioned gas detecting apparatus according to the present invention, by way of example. In this case, it is known that the sum of respective concentrations of the constituent gases is equal to 5,000 ppm. When each of the constituent gases has a concentration of 5,000 ppm, the characteristic coefficients of each of the sensors 401 to 406 are given in the following table:

TABLE I

| Sensor No. | Characteristic coefficient (expressed in the unit $10^{-8}$ mho/ppm) | | | | | |
|---|---|---|---|---|---|---|
| | oxygen | hydrogen | nitrogen dioxide | carbon monoxide | water vapor | hydrocarbons |
| 401 | 1.82 | 0 | 0 | 0 | 0.79 | 0.62 |
| 402 | 0 | 1.98 | 0.61 | 0.76 | 0 | 0 |
| 403 | 0 | 0.24 | 1.78 | 0.24 | 0 | 0.24 |
| 404 | 0 | 1.96 | 0 | 1.58 | 0 | 0.41 |
| 405 | 0 | 0.80 | 0 | 1.42 | 0 | 1.72 |
| 406 | 0 | 0 | 0 | 0 | 1.80 | 0 |

The conductivity of each of the sensors 401 to 406 which has been varied by the oxygen, hydrogen, nitrogen dioxide, carbon monoxide, water vapor and hydrocarbons contained in the mixed gas, is obtained through the aid of a detection circuit and a calculation program (shown in EMBODIMENT III) and has a value shown in the following table:

TABLE II

| Sensor No. | 401 | 402 | 403 | 404 | 405 | 406 |
|---|---|---|---|---|---|---|
| element conductivity (expressed in the unit $10^{-5}$ mho) | 1.53 | 1.40 | 0.99 | 0.91 | 0.43 | 0.05 |

When respective concentrations (expressed in ppm) of the constituent gases $O_2$, $H_2$, $NO_2$, CO, $H_2O$ and $C_mH_n$ are expressed by $C_{O2}$, $C_{H2}$, $C_{CO}$, $C_{H2O}$ and $C_{CmHn}$, respectively, the following 6 simultaneous linear equations can be readily formed by using the characteristic coefficients shown in TABLE I.

$$1.82 \times 10^{-8} \cdot C_{O2} + 0.79 \times 10^{-8} \cdot C_{H2O} + \quad (6)$$
$$0.62 \times 10^{-8} \cdot C_{CmHn} = 1.53 \times 10^{-5}$$

$$1.98 \times 10^{-8} \cdot C_{H2} + 0.61 \times 10^{-8} \cdot C_{NO2} + \quad (7)$$
$$0.76 \times 10^{-8} \cdot C_{CO} = 1.40 \times 10^{-5}$$

$$0.24 \times 10^{-8} \cdot C_{H2} + 1.78 \times 10^{-8} \cdot C_{NO2} + \quad (8)$$
$$0.24 \times 10^{-8} \cdot C_{CO} + 0.24 \times 10^{-8} \cdot C_{CmHn} =$$
$$0.99 \times 10^{-5}$$

$$1.96 \times 10^{-8} \cdot C_{H2} + 1.58 \times 10^{-8} \cdot C_{CO} + \quad (9)$$
$$0.41 \times 10^{-8} \cdot C_{CmHn} = 0.91 \times 10^{-5}$$

$$0.80 \times 10^{-8} \cdot C_{H2} + 1.42 \times 10^{-8} \cdot C_{CO} + \quad (10)$$
$$1.72 \times 10^{-8} \cdot C_{CmHn} = 0.43 \times 10^{-5}$$

$$1.8 \times 10^{-8} \cdot C_{CmHn} = 0.05 \times 10^{-5} \quad (11)$$

These simultaneous equations are solved by calculating means (shown IN EMBODIMENT III) to determine the concentrations $C_{O2}$, $C_{H2}$, $C_{NO2}$, $C_{CO}$, $C_{H2O}$ and $C_{CmHn}$, which have values shown in the following table:

TABLE III

| Concentration of constutuent gas (expressed in parts per million) | $C_{O2}$ | $C_{H2}$ | $C_{NO2}$ | $C_{CO}$ | $C_{H2O}$ | $C_{CmHn}$ |
|---|---|---|---|---|---|---|
| | 300 | 1600 | 900 | 700 | 300 | 1200 |

EMBODIMENT II

Figure 12A:
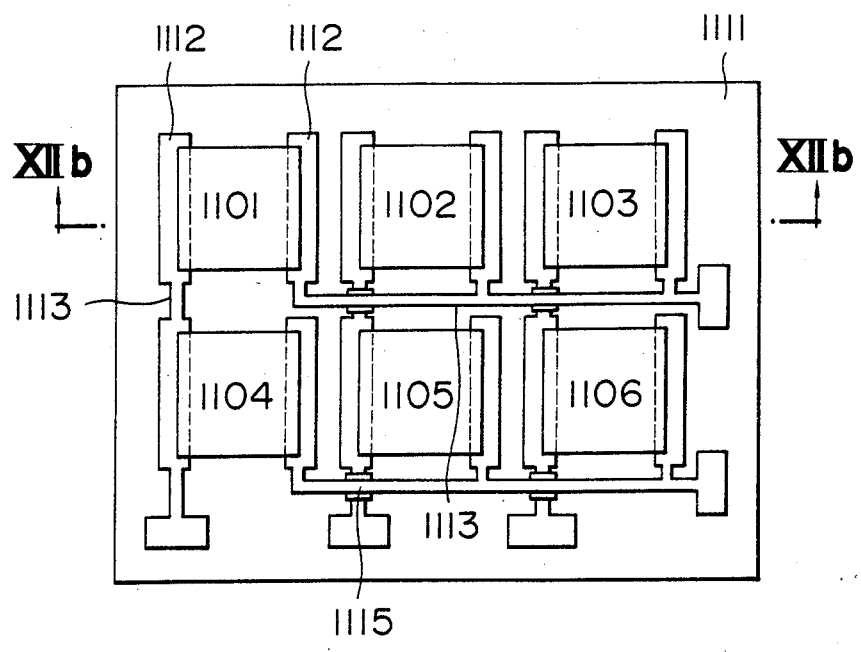
FIGS. 12a, 12b, 13a, 13b, 14a and 14b show various detecting element parts according to a second embodiment of the presnet invention which are different from the detecting element part shown in FIGS. 5a and 5b.
Figure 12B:
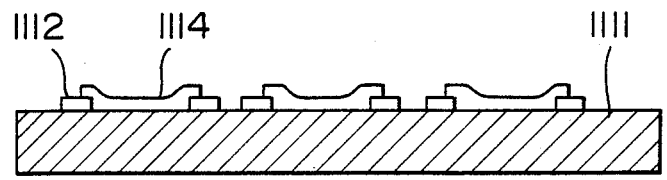

FIG. 12a is a plan view showing a gas detecting element part according to a second embodiment of the present invention, and FIG. 12b is a sectional view taken along the line $XII_b$ of FIG. 12a. As is apparent from FIG. 12a, six sensors 1101 to 1106 are arranged in the form of a matrix, and each sensor has a sheet-type structure to expose the detecting surface thereof to a detection gas. Further, electrodes are connected to each other in each row or in each column. A connecting conductor and another connecting conductor each for connecting electrodes are insulated from each other at the intersection of the connecting conductors by an insulating material for crossover.

The gas detecting element part shown in FIG. 12a can be formed in substantially the same manner as shown in EMBODIMENT I. First, gold paste (for example, paste No. 8760 manufactured by Dupont Co.) is applied to a heat-resisting, insulating substrate 1111 through the thick film printing technique so that electrodes 1112 and connecting conductors 1113 for connecting electrodes are formed. Then, a gas sensitive layer 1114 is made of six kinds of gas sensitive paste corresponding to six sensors.

Further, crystallized glass paste (for example, paste No. 9429 manufactured by Dupont Co.) is printed on that portion of a first connecting conductor which intersects with a second connecting conductor, to form an insulating layer 1115 for crossover, and then the second connecting conductor is printed. Thereafter, the above structure is heated at a predetermined temperature.

Figure 13A:
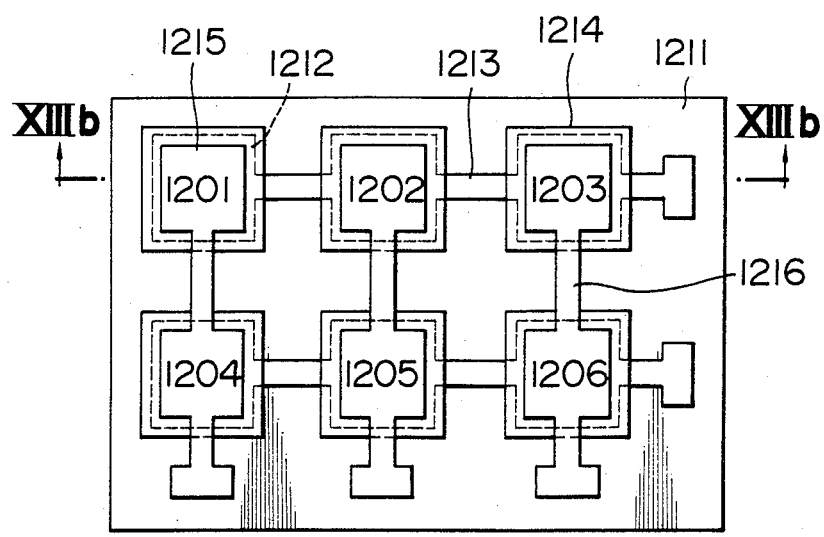
Figure 13B:
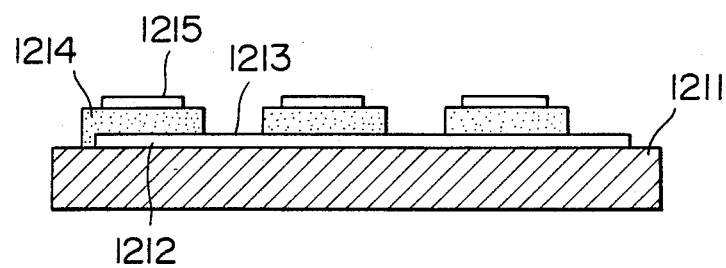
Figure 14A:
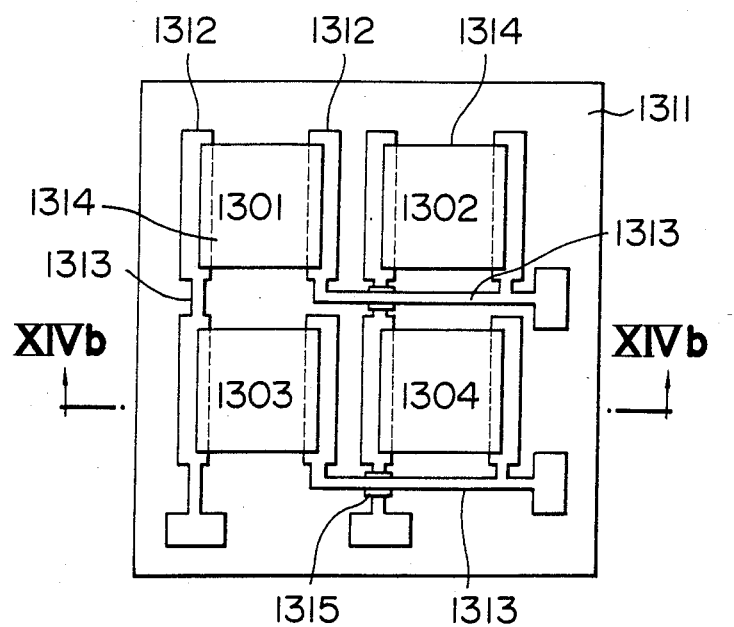
Figure 14B:
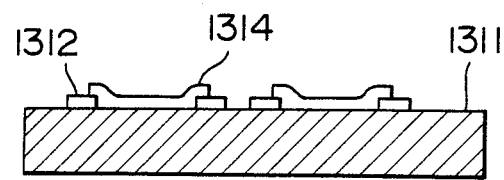

The detection output of each of the sensors 1101 to 1106 for each constituent gas was measured, and respective concentrations of the constituent gases were rapidly determined in the same manner as shown in EMBODIMENT 1. FIG. 13a shows a gas detecting element part which includes six sensors each having the same sandwich structure as shown in EMBODIMENT I but differs from EMBODIMENT I in wiring for connecting electrodes, and FIG. 13b is a sectional view taken along the line $XIII_b$ of FIG. 13a. FIG. 14a is a plan view showing a gas detecting element part having four sheet-type sensors for analyzing a mixed gas containing four constituent gases, and FIG. 14b is a sectional view taken along the line $XIV_b$ of FIG. 14a. The gas detecting element part shown in FIGS. 14a and 14b will be explained in brief. Gold electrodes 1312 and connecting conductors 1313 for connecting electrodes are deposited on a glass substrate 1311 through the evaporation technique, by the use of a mask.

Next, a gas sensitive layer 1314 is formed at each sensor by the sputtering method. The gas sensitive layers at sensors 1301, 1302, 1303 and 1304 are made of CoO, a mixture of ZnO and Pd, $Fe_3O_4$ and $SnO_2$, respectively. Further, when the electrodes and connecting conductors are formed, an $SiO_2$ film 1315 acting as an insulating layer is formed, by the sputtering method, on that portion of a first connecting conductor 1313 which intersects with a second connecting conductor 1313, and then second electrodes and second connecting conductors are deposited through the evaporation technique by the use of a mask. Thereafter, an integrated circuit is provided to amplify signal voltages.

Further, a microprocessor (shown in EMBODIMENT III) for processing the signal voltages is provided to obtain, by the real time processing, respective concentrations of constituent gases which are determined in the final stage of calculation.

In the above-mentioned explanation, a plurality of gas detecting materials which are different from each other in sensitivity for a specified constituent gas contained in a mixed gas, are used to form detecting elements, and the detecting elements are arranged on an insulating substrate to form a gas detecting element part. However, the sensitivity for the specified constituent gas can be made different not only by replacing a gas detecting material but also by changing the manufacturing method or manufacturing conditions of a gas detecting material. Further, although a plurality of sensors are arranged on an insulating substrate in the above explanation, discrete sensors may be united in one body. In these cases, gas information such as the kind and concentration of each of constituent gases contained in a mixed gas can be obtained by using the same software.

As mentioned above, by the use of a sensor unit for analyzing a multi-component gas according to the present invention, a plurality of constituent gases contained in a mixed gas can be quantitatively determined precisely and rapidly.

Further, since a signal processing circuit can be formed on the insulating substrate, real time signal processing can be performed. Moreover, a gas detecting apparatus provided with a simple, inexpensive sensor unit for analyzing a multi-component gas is obtained. Thus, the present embodiment can exhibit a remarkable effect in this field.

EMBODIMENT III

The circuit configuration of a gas detecting apparatus provided with one of sensor units described in EMBODIMENT's I and II and a method of processing detection signals from this sensor unit will be explained below.

Figure 15:
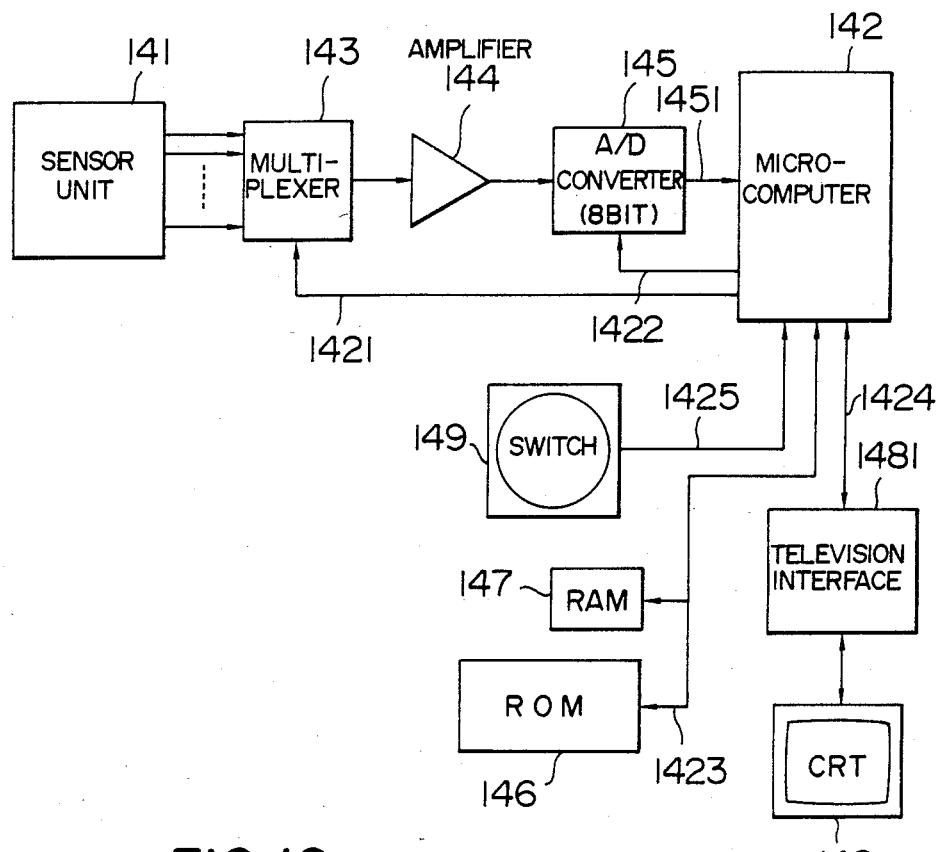
FIG. 15 is a block diagram showing a gas detecting apparatus according to the second embodiment of the present invention.
Figure 16:
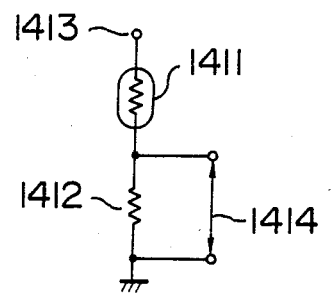
FIG. 16 is a circuit diagram showing a measuring circuit provided for each sensor of the sensor unit showin in FIG. 15.

FIG. 15 is a block diagram showing the outline of a gas detecting apparatus according to the present invention. Referring to FIG. 15, a sensor unit 141 is one of the sensor units described in EMBODIMENT's I and II, and a sensor 1411 included in the sensor unit 141 is connected in series with a fixed resistor 1412 as shown in FIG. 16. When the conductivity of the sensor 1411 is changed due to the detection of gas, a current flowing from a power source 1413 into the series combination of the sensor 1411 and fixed resistor 1412 is varied, and thus a potential difference 1414 across the fixed resistor 1412 is also varied. The above-mentioned detection signal means the potential difference 1414. Potential differences from sensors are successively selected by a multiplexer 143 which is controlled by a control signal 1421 from a microcomputer 142, to be voltage-amplified appropriately by an operational amplifier 144, and then converted into a digital signal by an A-D converter 145 which is controlled by a control signal 1422 from the microcompuer 142. The digital singal from the A-D converter 145 is supplied to the microcomputer 142. The calculation for the digital signal will be explained later in detail. A calculation program is previously stored in an ROM 146. The contents of the program are successively read in the microcomputer 142 through a bus line 1423, in accordance with the processing procedure in the microcomputer 142. A numerical value which has to be temporarily stored in any means in the course of the calculation, is sent through the bus line 1422 to an RAM 147, to be stored therein. The numerical value thus stored in supplied to the microcomputer 142 through the bus line 1423 at need. The results obtained at the end of calculation performed in the microcomputer 142 are sent to a television interface 1481, to be subjected to pre-processing, and are then displayed on the display screen of a CRT 148. A program for indicating the number and kind of data to be displayed by the CRT 148 and for indicating their display format is previously stored in the ROM 146. Further, an external selecting switch 149 is connected to the microcomputer 142 through a bus line 1425, to select one of an appropriate number of numerical values which are previously stored in the ROM 146 to be used as a special constant, that is, a characteristic value necessary to the calculation performed in the microcomputer 142.

Figure 17:
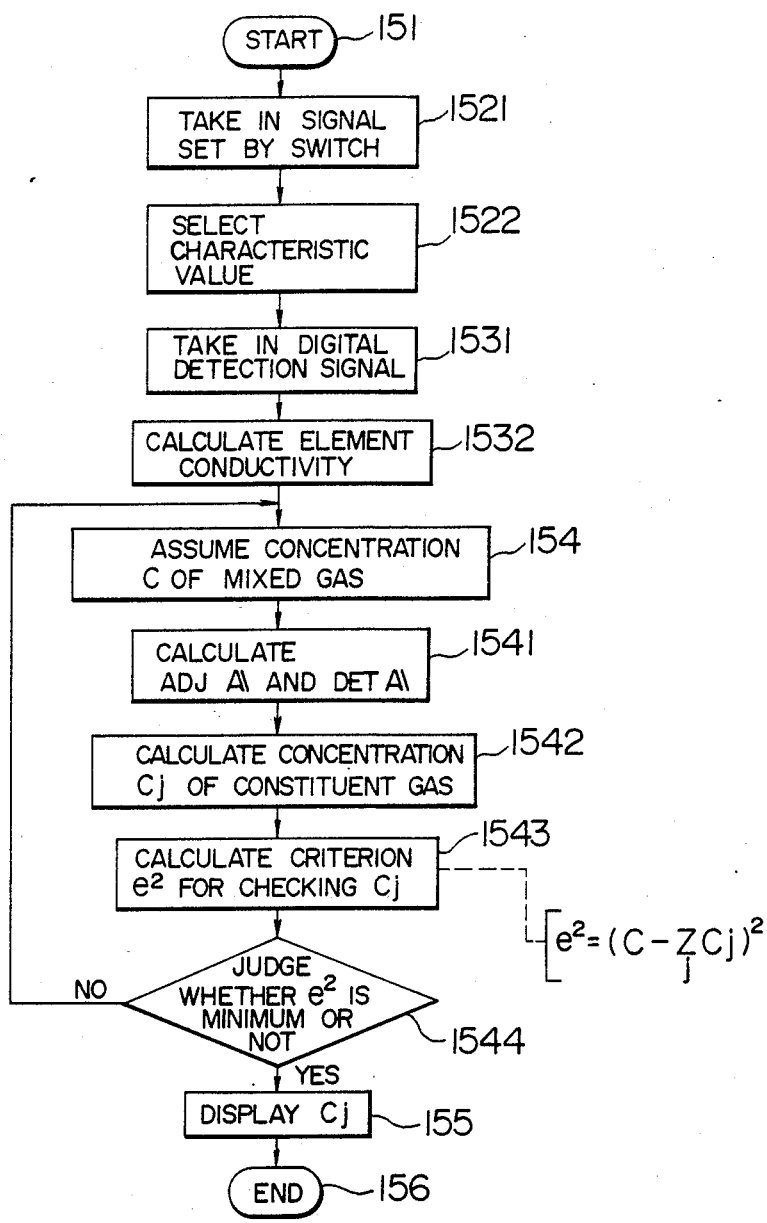
FIG. 17 is a flow chart showing operational processing performed in a gas detecting apparatus in accordance with a third embodiment of the present invention.

Next, explanation will be made of the calculatoin program executied in the microcomputer, with reference to FIG. 17.

When an instruction "START" is issued in step 151, the microcomputer first takes in a signal set by the switch 149 (step 1521). An address storing a numerical value used as the characteristic value is indicated by the set signal to select the numerical value as the characteristic value (step 1522). Next, the microcomputer takes in a digital detection signal by controlling the multiplexer 143 and A-D converter 145 (step 1531). The element conductivity of the sensor 1411 is calculated on the basis of the digital detection signal and circuit constants of the detection circuit shown in FIG. 16 such as the resistance of the resistor 1412 (step 1532). The above circuit constants are previously stored in the ROM 146.

As indicated by Equation (4), each of the characteristic coefficients used in the simultaneous equations is not a constant but a function of the concentration C of mixed gas. Therefore, it seems difficult to solve the simultaneous equations. However, this difficulty can be overcome in the following manner. That is, a numerical value is properly assumed for the concentration C of mixed gas (step 154). Next, the adjust matrix adj A and the determinant det A are calculated (step 1541), and then the concentration $C_j$ of each constituent gas is calculated (step 1542). Further, in step 1543, a criterion $e^2$ for checking the concentration $C_j$ is calculated by an equation $e^2 = (C - C_j)^2$. Then, the value of the concentration C is changed, so that the criterion $e^2$ decreases, and the above-mentioned processes are repeated each time the value of the concentration C is changed. That is, a value of the concentration $C_j$ which makes minimum the value of the criterion $e^2$, is determined by the method of successive approximation, to be used as an approximate value of the concentration $C_j$ (step 1544). The concentration $C_j$ thus determined and other desired results of calculation are displayed (step 155), and thus the calculation is completed (step 156).

According to the above-mentioned circuit configuration and calculation method, respective concentrations of constituent gases contained in a mixed gas can be determined which are not obtained by a conventional gas detecting apparatus provided with detecting elements, and moreover the calculation for determining the above concentrations can be performed rapidly and in a real time fashion. Further, the kind of signals set by the external selecting switch 149 can be incrased in accordance with the capacity of the ROM 146, and therefore various mixed gases which are different from each other in combination of constituent gases, can be analyzed by selecting characteristic coefficients corresponding to constituent gases. In other words, various mixed gases can be analyzed by a simple switching operation, and thus the present embodiment is of universal use and low in cost.

EMBODIMENT IV

In order to make up a gas detecting apparatus according to the present invention in which the effect of alcohol vapor on detection output is removed by calculation to determine respective concentrations of town gas (for example, methane) and carbon monoxide rapidly and precisely, an alcohol vapor detecting material for detecting only alcohol vapor is required. In the present embodiment, lanthanum-nickel oxide $LaNiO_3$ is used to detect only alcohol vapor. Furhter, two detecting elements are necessary to determine respective concentrations of methane and carbon monoxide, and at least one of the two detecting elements is required to be made of a material capable of detecting both of methane and carbon monoxide. In the present embodiment, tungsten oxide $WO_3$ which does not act with methane but can detect both of carbon monoxide and alcohol vapor, is used to form one of the two detecting elements, and tin oxide $SnO_2$ capable of detecting all of methane, carbon monoxide and alcohol vapor is used to form the other detecting element.

Now, the detection characteristic of $LaNiO_3$ will be explained below in detail. When this material is put in contact with a strongly deoxidizing gas such as alcohol vapor at a temperature in the vicinity of 300° C., oxygen in the material is taken away, and an M—O—M bond is severed. Thus, the conductivity of the material is decreased. However, when the alcohol vapor is removed, the material takes an original composition, and therefore has an original conductivity. It is a characteristic feature of $LaNiO_3$ that the above-mentioned phenomenon occurs only for alcohol vapor, and this material never acts with such gases as hydrogen methane, propane, isobutane, and carbon monoxide. Owing to these properties, $LaNiO_3$ is used as a practical material for detecting only alcohol vapor.

Next, methods of preparing three kinds of paste will be explained.

(a) Preparation of $LaNiO_3$ paste

La acetate and Ni acetate which have been concentrated to dryness, are heated at 600° C. in air to be decomposed, and then fired at 1000° C. in air to obtain a polycrystalline solid matter of $LaNiO_3$. The solid material is crushed and pulverized to obtain a fine, black $LaNiO_3$ powder. Then, 6 cc of an organic vehicle is added to 10 g of $LaNiO_3$ powder, and the mixture thus obtained is mixed with crystallized glass of Si—Pd—Zn—Ti series in the ratio of 10:1 by weight, to make $LaNiO_3$ paste.

(b) Preparation of $WO_3$ paste

A 99.99% pure $WO_3$ powder having a diameter less than 1 μm is used as the main component of $WO_3$ paste. 18 g of the $WO_3$ powder, 0.2 g of Pd powder, 2 g of binder glass and 7 cc of 9% tridecanol solution of ethyl cellulose having a viscosity of 10 cps are mixed, and the mixture is kneaded to make as sensitive paste.

(c) Preparation of $SnO_2$ paste 99.99% pure metallic tin is treated with concentrated nitric acid. After rinsed, a white precipitate of stannic acid is evaporated to dryness. Then, the precipitate is crushed and pulverized, and roasted at 700° C. in air to obtain an $SnO_2$ powder. An aqueous solution of $PdCl_2$ is added to the $SnO_2$ powder and the mixture is kneaded, to obtain the powder of a mixture containing $SnO_2$ and Pd in the ratio of 100:1 by weight. The powder thus obtained is treated in the same manner as in the $LaNiO_3$ paste, to make gas sensitive paste.

Now, explanation will be made of a gas detecting element part in which three kinds of paste prepared in the above-mentioned manner are used to form detecting elements.

Figure 18A:
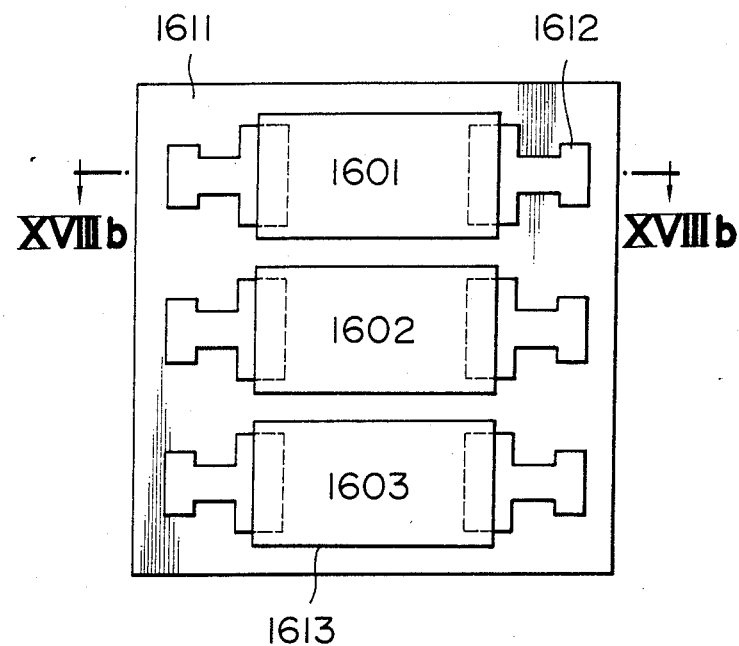
FIG. 18a is a schematic plan view showing a detecting element part according to a fourth embodiment of the present invention which includes three sensors.

FIG. 18a is a plan view showing a gas detecting element part which is the main point of the present embodiment. In the gas detecting element part are arranged three detecting elements (namely, sensors) 1601, 1602 and 1603 which are made of $LaNiO_3$ paste, $WO_3$ paste and $SnO_2$ paste, respectively. These sensors are fabricated in the following manner. Gold paste (for example, paste No. 8760 manufactured by Dupont Co.) is applied to a heat-resisting, insulating substrate 1611 through the thick film printing technique so that six electrodes 1612 are formed at predetermined positions, and then fired at 1200° C. for 2 hours. Next, each sensor paste 1613 is applied between predetermined electrodes 1612 through the thick film printing technique, and then fired at 900° C. for 10 minutes. Finally, predetermined wiring is formed to complete a gas detecting sensor unit.

Figure 18B:
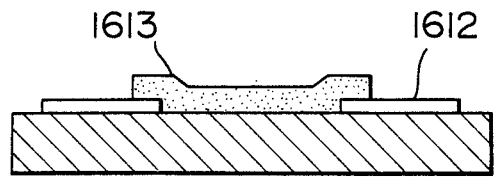
Figure 19:
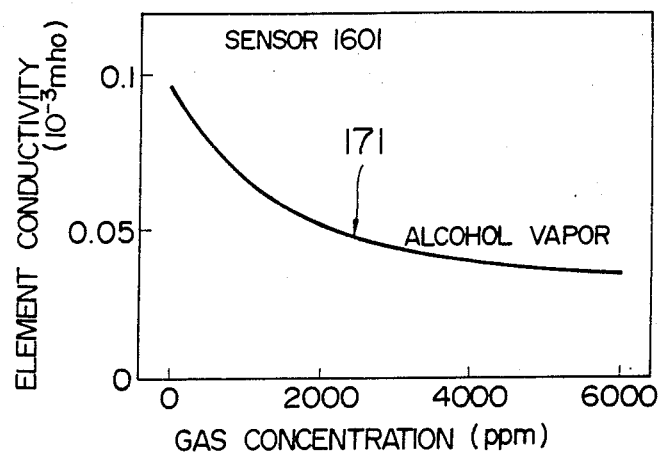
FIGS. 19 to 21 are graphs showing the detection characteristic of each of the sensors shown in FIG. 18a for a mixed gas containing three constituent gases.
Figure 20:
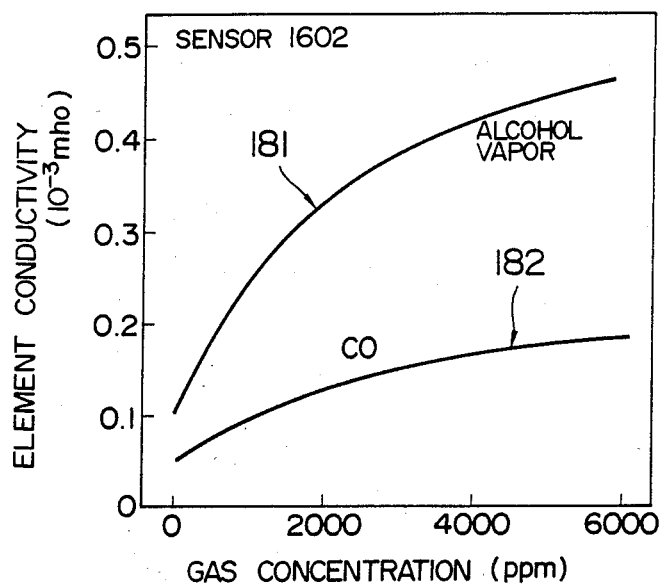
Figure 21:
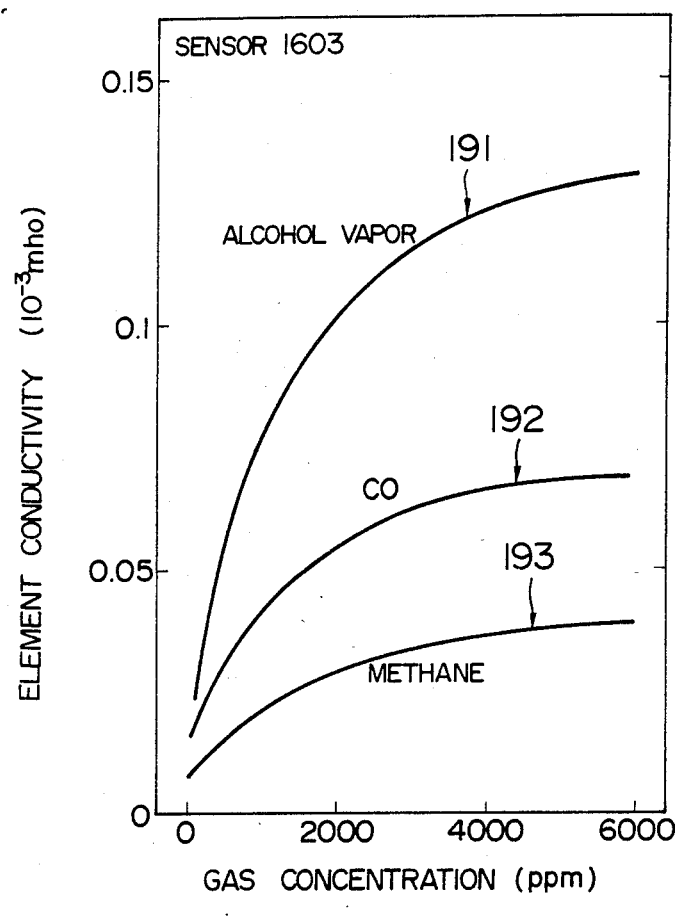

FIG. 18b is a sectional view of the sensor unit, taken along the line XVIII$_b$ shown in FIG. 18a. FIGS. 19 to 21 show the detection characteristics of the sensor unit. In FIG. 19, a curve 171 indicates a detection characteristic of the sensor 1601 for alcohol vapor. In FIG. 20, curves 181 and 182 indicate a detection characteristic of the sensor 1602 for alcohol vapor and that for carbon monoxide, respectively. In FIG. 21, curves 191, 192 and 193 indicate a detection characteristic of the sensor 1603 for alcohol vapor and those for carbon monoxide and methane, respectively.

The detection characteritics of the sensors 1601, 1602 and 1603 shown in FIGS. 19 to 21 can be expressed by the following equation:

$$g = k(C+l)^m \qquad (12)$$

At this time, the parameters k, l and m take values shown in the following table, in other words, characteristic values shown in the table are used in Equation (12).

TABLE IV

| Sensor No. | Detection gas | k | l | m |
|---|---|---|---|---|
| 1601 | alcohol vapor | 3.1 | 23 | −0.361 |
| 1602 | alcohol vapor | 0.351 | 31 | 0.336 |
|  | carbon monoxide | 0.144 | 150 | 0.387 |
| 1603 | alcohol vapor | 0.372 | 44 | 0.261 |
|  | carbon monoxide | 0.063 | 125 | 0.573 |
|  | methane | 0.143 | 320 | 0.337 |

Now, explanation will be made on the case where a mixed gas containing alcohol vapor, carbon monoxide and methane is analyzed by the use of the sensor unit according to the present embodiment, by way of example. In order to facilitate the explanation of the detection characteristics of each sensor for the mixed gas, various symbols will be used which are shown in the following table:

TABLE V

| Symbol | Contents |
|---|---|
| GL | a ratio of the element conductivity of the sensor 1601 for the mixed gas to a corresponding air level |
| GW | a ratio of the element conductivity of the sensor 1602 for the mixed gas to a corresponding air level |
| GS | a ratio of the element conductivity of the sensor 1603 for the mixed gas to a corresponding air level |
| gLA | a ratio of the element conductivity of the sensor 1601 for only alcohol vapor to a corresponding air level |
| gWA | a ratio of the element conductivity of the sensor 1602 for only alcohol vapor to a corresponding air level |
| gWC | a ratio of the element conductivity of the sensor 1602 for only carbon monoxide to a corresponding air level |
| gSA | a ratio of the element conductivity of the sensor 1603 for only alcohol vapor to a corresponding air level |
| gSC | a ratio of the element conductivity of the sensor 1603 for only carbon monoxide to a corresponding air level |
| gSM | a ratio of the element conductivity of the sensor 1603 for only methane to a corresponding air level |
| αW | a weighting factor relating to $G_W$ |
| αS | a weighting factor relating to $G_S$ |

Incidentally, a symbol g with suffix indicates ratio of an element conductivity obtained when a gas has a concentration C, to an element conductivity obtained when the concentration of the gas is zero (hereinafter referred to as "air level").

Each of the symbols gLA, gWA, gWC, gSA, gSC and gSM is used as the left-hand side of Equation (12), and values of the factors k, l and m corresponding to each of the above symbols are shown in TABLE IV.

Accordingly, the detection characteristic of each of the sensors 1601, 1602 and 1603 according to the present embodiment for the mixed gas is given by the following equations:

$$G_L = gLA \quad (13)$$
$$G_W = \alpha W(gWA + gWC - 1) + (1 - \alpha W) gWA \cdot gWC \quad (14)$$
$$G_S = \alpha S(gSA + gSC + gSM - 1) + (1 - \alpha S)gSA (gSC + gSM) \quad (15)$$

Further, the detection output of each sensor was measured, and the following values were obtained:

$$G_L = 0.21 \quad (16)$$
$$G_W = 4.98 \quad (17)$$
$$G_S = 7.90 \quad (18)$$

When respective concentrations of alcohol vapor, carbon monoxide and methane contained in the mixed gas are expressed by $C_A$, $C_C$ and $C_M$, respectively, these concentrations are obtained from Equations (13) to (18) in the following manner. First, the concentration $C_A$ is calculated from Equations (13) and (16), and the quantity gWA is determined from the concentration $C_A$. Then, the quantity gWA thus determined and Equation (17) are substituted in Equation (14), to determine the concentration $C_C$. Thereafter, Equation (18) and the quantities gSA and gSC respectively calculated from the concentrations $C_A$ and $C_C$ are substituted in Equation (15) to determine the concentration $C_M$. The abovementioned calculation is fairly complicated, but a univocal solution can be obtained for each of the concentrations $C_A$, $C_C$ and $C_M$. Thus, the following concentrations were obtained:

$$C_A = 1500 \text{ ppm} \quad (19)$$
$$C_C = 500 \text{ ppm} \quad (20)$$
$$C_M = 2000 \text{ ppm} \quad (21)$$

As mentioned above, according to the sensor unit of the present embodiment, the effect of alcohol vapor on the detection outputs of the sensor unit can be removed by calculation, and thus respective concentrations of constituent gases contained in a mixed gas can be determined precisely, even when alcohol vapor is contained in the mixed gas. Therefore, the present embodiment can provide a simple, inexpensive sensor unit for analyzing a multi-component gas.

EMBODIMENT V

The circuit configuration of a gas detecting apparatus provided with the sensor unit described in EMBODIMENT IV and a method of processing detection signals from the sensor unit will be explained below.

Figure 22:
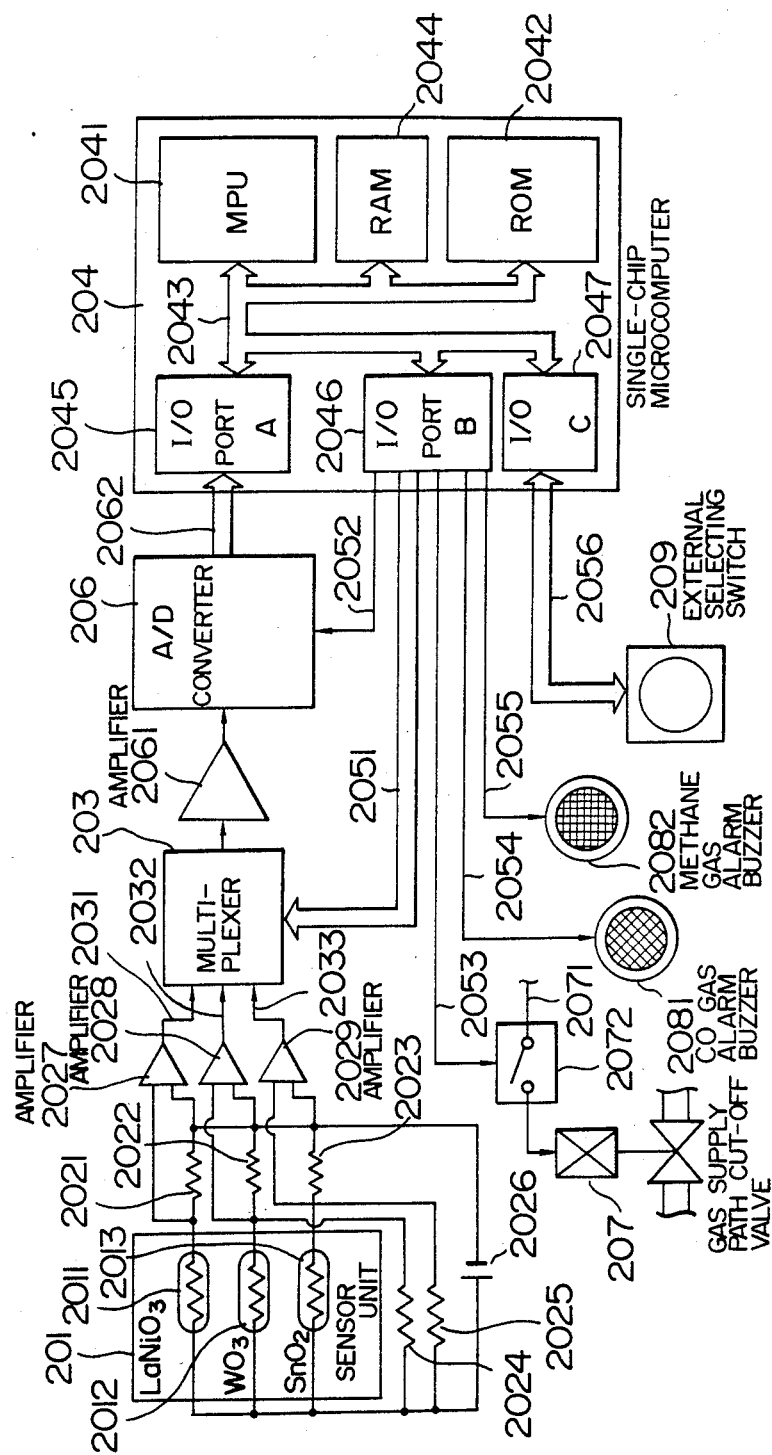
FIG. 22 is a block diagram showing a gas detecting apparatus according to a fifth embodiment of the present invention.

FIG. 22 is a block diagram showing the outline of a gas detecting apparatus according to the present invention. Referring to FIG. 22, a sensor unit 201 includes sensors 2011, 2012 and 2013 which are made of three materials $LaNiO_3$, $WO_3$ and $SnO_2$ described in EMBODIMENT IV, respectively. The sensors 2011, 2012 and 2013 are connected in series with fixed resistors 2021, 2022 and 2023, respectively, and further the sensors 2012 and 2013 are connected in parallel with fixed resistors 2024 and 2025, respectively. When the element conductivity of each sensor is changed due to the detection of gas, a current flowing from a power source 2026 into a circuit made up of each sensor and one or two fixed resistors connected thereto is changed, and thus potential differences across the fixed resistors 2021, 2022 and 2023 are varied. The potential differences are amplified by operational amplifiers 2027, 2028 and 2029, which deliver analog signals 2031, 2032 and 2033, respectively. The three analog signals are successively selected by a multiplexer 203 which is controlled by a control signal 2051 from a microcomputer 204, to be successively amplified by an operational amplifier 2061, and are then converted into a digital signal 2062 by an A-D converter 206 which is controlled by a control signal 2052 from the microcomputer 204. A method of processing input signals of the microcomputer such as the digital signal 2062 will be explained later in detail. Now, the inner structure of the microcomputer 204 will be explained below.

All operations in the microcomputer 204 is controlled by an MPU (namely, microprocessor) 2041. Mechanical programs processed in the MPU 2041 are previously stored in an ROM 2042, and are successively supplied to the MPU 2041 through a bus line 2043. Furhter, numerical values which are obtained in the course of the processing and have to be temporarily stored, are sent through the bus line 2043 to an RAM 2044 to be stored therein. The microcomputer 204 exchanges signals with peripheral parts through an I/O port A 2045, an I/O port B 2046 and an I/O port C 2047, each of which has an appropriate number of bits. The previously-mentioned digital signal 2062 is transfered to the MPU 2041 through the I/O port A 2045 and bus line 2043. The control signals 2051 and 2052 are sent out from the MPU 2041, and pass through the I/O port B 2046.

Further, decision signals for blocking up a gas supply path and for generating alarms are generated on the basis of the results of calculation performed in the MPU 2041. These decision signals pass through the I/O port B 2046, and are then delivered as control signals 2053, 2054 and 2055. The control signal 2053 controls a contact change-over element (namely, an electromagnetic relay) 2072 in a power circuit 2071 for driving a gas supply path cut-off valve 207, so that the valve 207 is usually kept open and is closed when there are leaks of gas. On the other hand. the control signal 2054 causes a CO alarm buzzer 2081 to vibrate when carbon monoxide is generated, and the control signal 2055 causes a methane alarm buzzer 2082 to vibrate when methane gas leaks out.

Further, an external selecting switch 209 is connected to the MPU 2041 through a bus line 2056, the I/O port C 2047 and the bus line 2043. The characteristic values in Equation (2), the weighting factors in Equations (14) and (15), and criterions for generating the previously-mentioned decision signals are all used in the calculation performed in the microcomputer 204. Each of some of the above-mentioned characteristic values, weighting factors and criterions can be selected, by the external selecting switch 209, from an appropriate number of numerical values which are previously stored in the ROM 2042.

Figure 23:
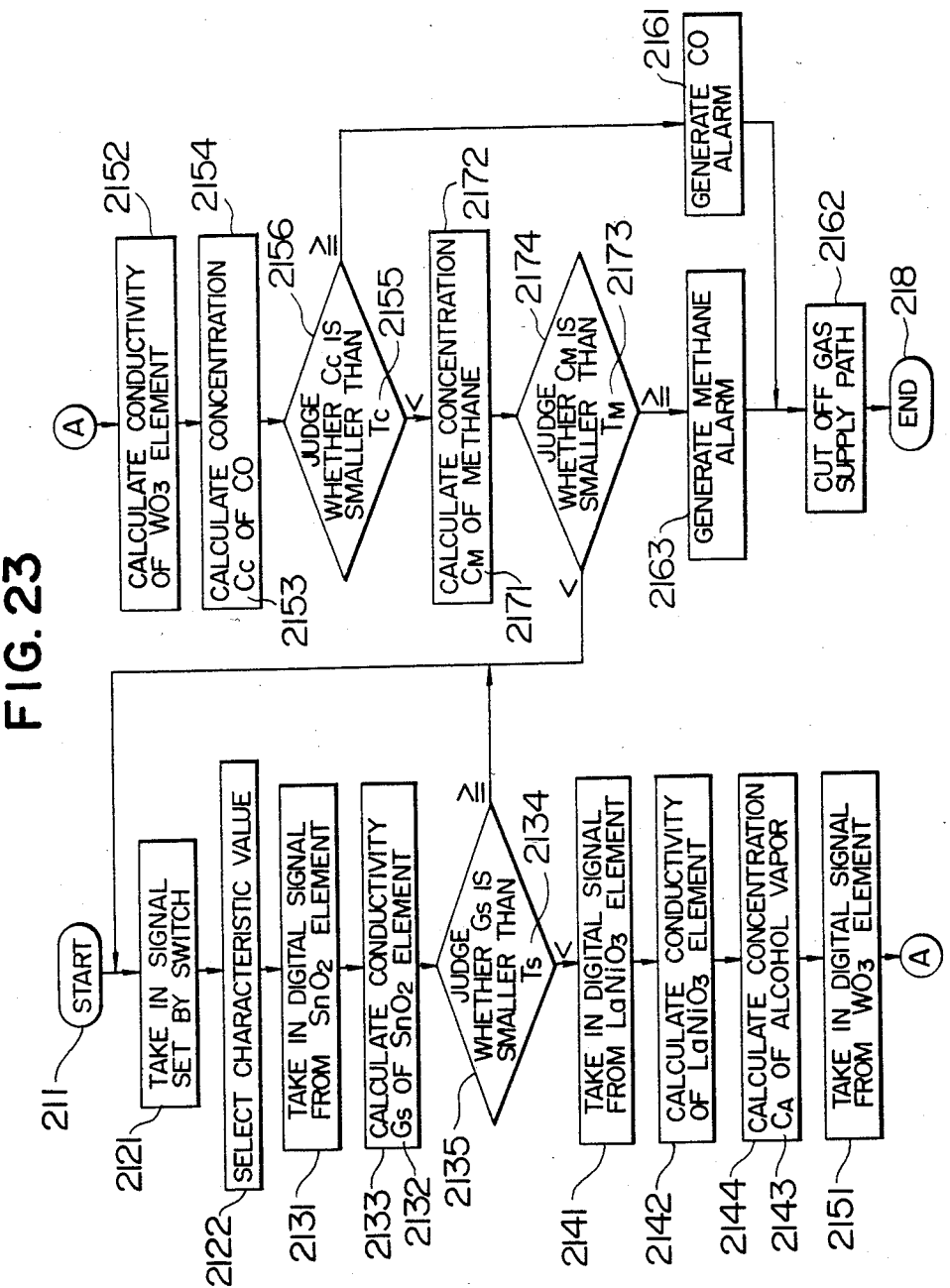
FIG. 23 is a flow chart showing operational processing performed in the gas detecting apparatus shown in FIG. 22.

Next, a calculation program of the present embodiment which is executed by the microcomputer 204, will be explained below, with reference to FIG. 23. When an instruction "START" is issued in step 211, the microcomputer first takes in a signal set by the switch 209 (step 2121). An address storing a numerical value used as the characteristic value is indicated by the set signal to select the numerical value as the characteristic value (step 2122). Next, the microcomputer takes in a digital detection signal from the $SnO_2$ element 2013, by controlling the multiplexer 203 and A-D converter 206 (step 2131). The conductivity $G_S$ (indicated by reference numeral 2132) of the $SnO_2$ element 2013 is calculated on the basis of the above-mentioned digital detection signal and circuit constants of a measuring circuit connected to the sensor unit 201 such as the resistance values of the resistors 2023 and 2025 (step 2133). The above circuit constants are previously stored in the ROM 2042. Then, it is judged whether a criterion Ts (indicated by reference numeral 2134) for generating the methane alarm, that is, a minimum conductivity of the $SnO_2$ element requiring the methane alarm is larger than the conductivity $G_S$ or not (step 2135). The criterion Ts is previously stored in the ROM 2042. When the conductivity $G_S$ is smaller than the criterion $T_S$, the step 2121 and the following steps are repeated. When the conductivity $G_S$ is greater than or equal to the criterion $T_S$, the following processing is performed.

First, the microcomputer takes in a digital detection signal from the $LaNiO_3$ element 2011 (step 2141). Similarly to step 2133, the conductivity of the $LaN_iO_3$ element is calculated on the basis of the abovementioned digital detection signal and the resistance value of the resistor 2021 (step 2142). Then, the concentration $C_A$ (indicated by reference numeral 2143) of alcohol vapor is calculated from the calculated value of the conductivity of the $LaNiO_3$ element 2011 (step 2144).

Next, the microcomputer takes in a digital detection signal from the $WO_3$ element 2012 (step 2151). In step 2152, the conductivity of the $WO_3$ element 2012 is calculated on the basis of the above-mentioned digital detection signal and the resistance values of the resistors 2022 and 2024 in the same manner as in step 2133. Then, the concentration $C_C$ (indicated by reference numeral 2153) of carbon monoxide is calculated from the calculated value of the conductivity of the $WO_3$ element 2012 (step 2154). In step 2156, it is judged whether a criterion $T_C$ (indicated by reference numeral 2155) for generating the CO alarm, that is, a minimum concentration of carbon monoxide requiring the CO alarm is larger than the concentration $C_C$ or not. The criterion $T_C$ is previously stored in the ROM 2042. When the concentration $C_C$ is greater than or equal to the criterion $T_C$, the CO alarm is generated (step 2161) and the gas supply path is blocked (step 2162). Thus, the calculation is completed (step 218). When the concentration $C_C$ is smaller than the criterion $T_C$, the following processing is performed.

The concentration $C_M$ (indicated by the reference numeral 2171) of methane is calculated from the conductivity 2132 of the $SnO_2$ element 2013 (step 2172). Then, it is judged whether a criterion $T_M$ (indicated by reference numeral 2173) for generating the methane alarm, that is, a minimum concentration of methane requiring the methane alarm is larger than the concentration $C_M$ or not (step 2174). The criterion $T_M$ is previously stored in the ROM 2042. When the concentration $C_M$ is greater than or equal to the criterion $T_M$, the methane alarm is generated (step 2163), and the gas supply path is blocked (step 2162). Thus, the calculation is completed (step 218). When the concentration $C_M$ is smaller than the criterion $T_M$, the step 2121 and the following steps are repeated.

As mentioned above, the calculation is completed in step 218, immediately after one of the alarms has been generated in step 2161 or 2163 on the basis of the results of judgment in step 2156 or 2174 and the gas supply path has been blocked in step 2162. However, the control signals 2053, 2054 and 2055 are held even after the calculation has been completed, and therefore the state of the gas supply path cut-off valve 207 and the operation of the alarm buzzers 2081 and 2082 are kept unchanged. In the case where the step 2121 and the following steps are repeated after the processing in step 2162 to carryout endless processing, the gas supply path is made open and the alarm buzzers are stopped as soon as the concentrations $C_C$ and $C_M$ become less than the criterions $T_C$ and $T_M$, respectively.

Further, in the case where each of the criterions $T_C$ and $T_M$ is expressed stepwise by a plurality of numerical values and a plurality of judgments corresponding to these numerical values are successively carried out, it is possible to generate different alarms in accordance of the concentration of gas.

Although the non-linear detection characteristic is caused by alcohol vapor as in the present embodiment, ambient temperature or humidity may cause a non-linear detection characteristic. In this case, a temperature or humidity sensitive element is included in a sensor unit, and outputs from the sensor unit are processed so that the effect of temperature or humidity on the detection outputs is removed, to obtain corrected values for respective concentrations of constituent gases.

According to the gas detecting apparatus and calculation method explained in the above description, it is possible to determine respective concentrations of carbon monoxide and methane without being disturbed by alcohol vapor, though such determination cannot be made by a conventional gas detecting apparatus provided with detecting elements. Further, the above-mentioned concentrations can be rapidly calculated by real time processing. Therefore, it is evident that the present embodiment exhibits a remarkable effect. Further, the above-mentioned apparatus for and method of determining respective concentrations of constituent gases are not known in all the countries of the world.

Further, since various characteristic values can be set by the external selecting switch, respective concentrations of constituent gases contained in each of various kinds of mixed gases, for example, various town gases used in our country can be determined by selecting characteristic values by the switch in accordance with the town gas to be analyzed. Accordingly, a gas detecting apparatus accordingto the present embodiment is of universal use, and moreover can be mass-produced.

As has been explained in the foregoing, a gas detecting apparatus accordingto the present invention can determine respective concentrations of constituent gases contained in a multi-component gas, precisely and rapidly.

Further, according to the present invention, the quantitative analysis of a multi-component gas can be made with a single apparatus, and therefore a simple, inexpensive gas detecting apparatus is obtained. Thus, the present invention exhibits a remarkable effect in this field.

What we claim is:

1. A gas detecting apparatus for detecting at least one kind of specified constituent gas in a mixed gas made up of a plurality of kinds of constituent gases, comprising:
   (a) a plurality of semiconductor gas detecting elements different from each other in a gas detection characteristic based on the conductivity of the element, said detection characteristic of each gas detecting element being exponential to gas concentration and detection outputs from said gas detecting elements with respect to the mixed gas being represented by a linear combintion of said detection outputs with respect to said constituent gases;
   (b) a processing device receiving detection outputs from said semiconductor gas detecting elements for processing said detection outputs and previously-stored characterisitc values, said characteristic values indicating a characteristic of each of said semiconduttor gas detecting elements for the mixed gas, said processing device using a linear operation; and
   (c) output means operated on the basis of the results of processing performed in said processing device.

2. A gas detecting apparatus according to claim 1, wherein said processing device includes (a) storage means for storing therein said characteristic values of said semiconductor gas detecting elements for said mixed gas and a calculation program, (b) processing means for executing said calculation program, (c) a multiplexer for selecting one of detection outputs from said semiconductor gas detecting elements based on a control signal from said processing means; and (d) an analog-to-digital converter applied with a selected detection output from said multiplexer for converting said selected detection output into a digital signal, said digital signal being supplied to said processing means.

3. A gas detecting apparatus according to claim 2, wherein external selecting means connected to said processing means is used to select a specified characteristic value from said characteristic values stored in said storage means.

4. A gas detecting apparatus according to claim 1, wherein said output means is a cathode ray tube for displaying the results of operational processing performed in said processing device.

5. A gas detecting apparatus according to claim 1, wherein said output means is an alarm means which is operated when presence of a specified constituent gas is detected by said processing device.

6. A gas detecting apparatus according to claim 1, wherein said output means is alarm means which is operated when a specified concentration of a specified constituent gas is detected by said processing device.

7. A gas detecting apparatus according to claim 1, wherein said output means is one of gas supply cut-off means and gas diluting means which are operated when presence or a specified concentration of a specified constituent gas is detected by said processing device.

8. A gas detecting apparatus according to claim 1, wherein said semiconductor gas detecting elements include a first detecting element for detecting only alcohol vapor, a second detecting element for detecting alcohol vapor and carbon monoxide, and a third detecting element for detecting alcohol vapor, carbon monoxide and methane.

9. A gas detecting apparatus according to claim 8, wherein said first, second and third detecting elements are made of lanthanum-nickel oxide, tungsten oxide and tin oxide, respectively.

* * * * *